(12) United States Patent
Nguyen-Demary et al.

(10) Patent No.: US 10,166,137 B2
(45) Date of Patent: Jan. 1, 2019

(54) HIGH BARRIER ELASTOMER FECAL CATHETER OR OSTOMY POUCH

(75) Inventors: Tinh Nguyen-Demary, Milltown, NJ (US); Mingliang Lawrence Tsai, Holmdel, NJ (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 570 days.

(21) Appl. No.: 14/005,814

(22) PCT Filed: Mar. 16, 2012

(86) PCT No.: PCT/US2012/029375
§ 371 (c)(1),
(2), (4) Date: Mar. 26, 2014

(87) PCT Pub. No.: WO2013/043226
PCT Pub. Date: Mar. 28, 2013

(65) Prior Publication Data
US 2014/0288517 A1    Sep. 25, 2014

Related U.S. Application Data

(60) Provisional application No. 61/453,667, filed on Mar. 17, 2011.

(51) Int. Cl.
| | | |
|---|---|---|
| A61F 5/441 | (2006.01) |
| A61L 29/02 | (2006.01) |
| A61L 29/14 | (2006.01) |
| A61F 5/445 | (2006.01) |
| A61L 29/04 | (2006.01) |
| A61L 28/00 | (2006.01) |
| A61L 29/08 | (2006.01) |
| A61L 29/12 | (2006.01) |

(52) U.S. Cl.
CPC .............. *A61F 5/441* (2013.01); *A61F 5/445* (2013.01); *A61L 28/003* (2013.01); *A61L 28/0026* (2013.01); *A61L 28/0069* (2013.01); *A61L 28/0092* (2013.01); *A61L 29/02* (2013.01); *A61L 29/049* (2013.01); *A61L 29/085* (2013.01); *A61L 29/126* (2013.01); *A61L 29/14* (2013.01); *A61L 2300/64* (2013.01); *A61L 2400/12* (2013.01); *A61L 2420/04* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 4,546,143 | A | * | 10/1985 | Weil | C08L 21/00 524/511 |
| 5,019,062 | A | * | 5/1991 | Ryan | A61F 13/8405 604/359 |
| 5,306,487 | A | * | 4/1994 | Karapasha | A61L 9/01 424/76.6 |
| 5,817,300 | A | * | 10/1998 | Cook | A61F 5/441 424/66 |
| 5,860,959 | A | * | 1/1999 | Gent | A61F 5/441 604/327 |
| 6,329,465 | B1 | * | 12/2001 | Takahashi | C08L 23/0815 525/191 |
| 6,485,476 | B1 | * | 11/2002 | von Dyck | A61F 5/441 600/29 |
| 6,605,304 | B1 | * | 8/2003 | Wellinghoff | A01N 25/18 424/489 |
| 6,617,016 | B2 | * | 9/2003 | Zhang | C08L 53/02 428/318.6 |
| 6,852,100 | B1 | * | 2/2005 | Gent | A61F 5/441 604/333 |
| 6,946,182 | B1 | * | 9/2005 | Allgeuer | B29C 43/222 264/134 |
| 6,946,522 | B2 | * | 9/2005 | Jacob | C08L 53/025 525/191 |
| 7,056,971 | B2 | * | 6/2006 | Varma | B65D 39/0017 524/490 |
| 7,060,753 | B2 | * | 6/2006 | Jacob | C08K 5/0008 525/191 |
| 7,629,406 | B2 | * | 12/2009 | Qian | C08L 23/06 524/261 |
| 2002/0055594 | A1 | * | 5/2002 | Roux | B01J 20/26 525/329.7 |
| 2006/0173430 | A1 | * | 8/2006 | Lee | A61F 5/4401 604/368 |
| 2007/0237916 | A1 | * | 10/2007 | Rasmussen | A61F 5/441 428/35.2 |

(Continued)

FOREIGN PATENT DOCUMENTS

| | | |
|---|---|---|
| EP | 0347746 A1 | 12/1989 |
| EP | 1690553 A1 | 8/2006 |

(Continued)

OTHER PUBLICATIONS

PCT/US2012/29375 International Preliminary Report on Patentability dated Sep. 17, 2013.
PCT/US2012/29375 Written Opinion completed Jun. 12, 2012.
PCT/US2012/29375 International Search Reportcompleted Jun. 12, 2012.
Acquarulo and O'Neil, Advances in compounding medical plastics with nanoclay fillers are pushing the materials envelope for minimally invasive devices. Enhancing Medical Device Performance with Nanocomposite Polymers, posted May 1, 2002, 4 pages. [Retrieved on Jan. 14, 2016; Retrieved from the Internet: http://www.mddionline.com/article/enhancing-medical-device-performance-nanocomposite-polymers].
Japanese Patent Application No. 2013-558199 Office Action dated Jan. 20, 2016.
Australian Patent Application No. 2012313393 Examiners Second Report dated Sep. 1, 2016.

(Continued)

*Primary Examiner* — Tatyana Zalukaeva
*Assistant Examiner* — Guy K Townsend
(74) *Attorney, Agent, or Firm* — Wilson Sonsini Goodrich & Rosati

(57) ABSTRACT

A fecal catheter or ostomy pouch made of an odor barrier material including a thermoplastic elastomer, odor barrier modifier and an antiblocking agent.

24 Claims, No Drawings

(56) References Cited

U.S. PATENT DOCUMENTS

| | | | | |
|---|---|---|---|---|
| 2008/0103463 A1* | 5/2008 | Tsai | ............ | A61F 5/445 604/317 |
| 2009/0088711 A1* | 4/2009 | Shelley | ............ | A61M 25/0045 604/328 |
| 2009/0216207 A1* | 8/2009 | Nielsen | ............ | C08J 5/18 604/328 |
| 2011/0052737 A1* | 3/2011 | Florence | ............ | A61K 8/97 424/742 |
| 2014/0288517 A1* | 9/2014 | Tsai | ............ | A61F 5/445 604/333 |

FOREIGN PATENT DOCUMENTS

| | | |
|---|---|---|
| GB | 2259858 A | 3/1993 |
| GB | 2329339 A | 3/1999 |
| JP | S59151965 A | 8/1984 |
| JP | H0924580 A | 1/1997 |
| JP | 2001061886 A | 3/2001 |
| JP | 2005307049 A | 11/2005 |
| JP | 2005533618 A | 11/2005 |
| WO | WO-9112029 A1 | 8/1991 |
| WO | WO-2009144486 A2 | 12/2009 |
| WO | WO 2013/043226 A1 | 3/2013 |
| WO | WO-2013030581 A1 | 3/2013 |

OTHER PUBLICATIONS

Chinese Patent Application No. 201280021995.9 Decision of Rejection dated Sep. 14, 2016.
European Patent Application No. 12833128.7 Communication dated Aug. 31, 2016.
Japanese Patent Application No. 2013-558199 Office Action dated Sep. 6, 2016.
Japanese Patent Application No. 2013-558199 Office Action dated Apr. 4, 2017.
New Zealand Patent Application No. 712149 Examiner's second report dated Mar. 8, 2017.
New Zealand Patent Application No. 712149 Further Examination Report dated May 2, 2017.
Australia Patent Application No. 2016228205 Examination Report No. 1 dated Jun. 7, 2017.
Chinese Patent Application No. 201280021995.9 Office Action dated May 25, 2017.
Chinese Patent Application No. 201280021995.9 Decision on Reexamination dated Jan. 3, 2018.
Chinese Patent Application No. 201280054020.6 Third Office Action dated Jul. 27, 2016.
European Patent Application No. 12756241.1 Communication dated Sep. 7, 2016.
PCT/GB2012/052133 International Preliminary Report on Patentability dated Mar. 4, 2014.
PCT/GB2012/052133 International Search Report and Written Opinion dated Dec. 14, 2012.
Russian Patent Application No. 2014112699 Official Action dated Aug. 22, 2016.
U.S. Appl. No. 14/347,970 Office Action dated Jun. 30, 2017.
U.S. Appl. No. 14/347,970 Office Action dated Nov. 30, 2016.
Australia Patent Application No. 2016228205 Examination Report No. 2 dated May 29, 2018.
Canadian Patent Application No. 2,834,848 Office Action dated Apr. 3, 2018.
Mexican Patent Application No. MX/a/2015/015197 Office Action dated Mar. 2, 2018.

* cited by examiner

HIGH BARRIER ELASTOMER FECAL CATHETER OR OSTOMY POUCH

CROSS-REFERENCE

This application is filed pursuant to 35 U.S.C. § 371 as a United States National Phase Application of International Application Ser. No. PCT/US2012/029375, filed Mar. 16, 2012, which claims the benefit of and the right of priority to U.S. Patent Application No. 61/453,667 filed Mar. 17, 2011, both of which are incorporated by reference herein in their entirety.

FIELD OF THE INVENTION

The present invention relates to an odor barrier material for a fecal catheter, a fecal pouch, or an ostomy pouch.

BACKGROUND OF THE INVENTION

Fecal catheters have occasionally been criticized for the transmission of fecal odor through the tubular walls. A possible cause of the poor odor barrier is the silicone material of which these devices are composed. The odor barrier of silicone is known to be one of the worst among polymer materials. For example, the oxygen transmission rate of silicone has been reported to be 775,000 cc mil/m$^2$/day. Therefore, a 20 mil thick silicone catheter is about 3 orders of magnitude worse than a commonly used ostomy film having a transmission rate of 50 cc/m$^2$/day or less.

Another possible explanation for silicone fecal catheter having poor odor barrier is that the extruded silicone utilized in such devices is relatively rough and as a result could trap fecal components. The contours of the spots trapping the fecal material provide substantial surface area, through which odor is transmitted. The combination of high odor transmission rate and large surface area contributes to the poor odor barrier characteristics of the silicone used in fecal catheters.

It would be desirable to develop a material to be used in a fecal catheter that has the desirable characteristics of silicone while providing an odor barrier substantially better than that of silicone.

It is the object of the present invention to provide an odor barrier polymer having these characteristics.

DESCRIPTION OF THE INVENTION

Thermoplastic elastomer (TPE) or curable elastomer is well known for use in medical devices. However, these elastomers are not known to exhibit high odor barrier properties. The present invention is the modification of elastomer to achieve a high odor barrier while maintaining its softness, ability for post extrusion converting (welding and bonding) and non-blocking characteristics.

One embodiment of the present invention related to single layer of catheter made from a high barrier elastomer such that the odor barrier measured by oxygen transmission rate per ASTM D3985 is not more than 50,000 cc mil/m$^2$/day at 23° C., or more preferably not more than 5,000 cc mil/m$^2$/day. Such a catheter is at least 10 times better in odor barrier than the silicone catheter.

U.S. Pat. Nos. 6,946,522, 7,056,971, and 7,060,753 disclosed the use of a liquid polyisobutene oil plasticizer to improve the gas barrier of the TPE. However, these formulations, especially when targeting a soft elastomer, i.e., Shore A less than 60, creates a blocking issue in which the surface of TPE catheter seals against each other upon folding and packaging. The use of a higher amount of oil plasticizer would allow a softer TPE, but it comes with an adverse effect in an oily surface, resulting in poor post-extrusion converting (welding and bonding). In addition, the TPE based on an olefin block copolymer (OBC, such as Infuse™ made by Dow) was not disclosed. Although common approaches exist to minimize the blocking, including adding mineral oil or slip additives. These approaches; however, have drawbacks in that they prevent the parts from being further converted into a fecal catheter due to their adverse effects on the surface bonding. U.S. Pat. No. 7,629,406 disclosed the use of an organoclay at a concentration less than 4% to improve the barrier properties of high density polyethyelene (HDPE). However, the use of organoclay in a TPE was not mentioned with a Shore A hardness not more than 60, or preferably not more than 50.

Another embodiment of the present invention is related to a fecal catheter, having a Shore A hardness not more than 60 and an oxygen transmission rate not more than 2,500 cc/m$^2$/day or preferably not more than 1,000 cc/m$^2$/day, comprising (1) a thermoplastic elastomer, (2) odor barrier modifier, and (3) an antiblocking agent of at least 0.1%, wherein thermoplastic elastomer is selected from the group consisting of a styrenic block copolymer, a thermoplastic vulcanizate, or a polyolefin elastomer, and wherein odor barrier modifier is selected from the group consisting of polyisobutene, polybutene, or an organoclay, and wherein the antiblocking agent is selected from the group consisting of an essentially inorganic fillers, such as silica, talc, clay, mica, etc. and blends thereof. It is noted organoclays can be used in one embodiment as both the odor barrier modifier and as the antiblocking agent. Organoclays include montmorillonite clay, smectite clay, intercalated clay, nanoclay, or a mixture of above. Organoclay described in this invention includes montmorillonite clay, made by Nanocor, which is the most common member of the smectite clay family. Organoclay may consist of nanoclay with a unique morphology such that one dimension is in the nanometer range. In addition, organoclay is preferred to be intercalated with an organic intercalant resulting in a clay-chemical complex wherein the clay gallery spacing has increased due to the process of surface modification. Under the proper conditions of temperature and shear, an intercalate is capable of exfoliating in a resin matrix. Optionally, the following additives can be used to facilitate the manufacturing of catheter extrusion, including melt viscosity modifier, tackifier, detackifier, plasticizer, etc.

Styrenic block copolymer (SBC) based thermoplastic elastomer includes styrene-isoprene-styrene (SIS), styrene-butadiene-styrene (SBS), styrene-etheylene/butylene-styrene (SEBS), styrene-etheylene/propylene-styrene (SEPS), and blends thereof. Thermoplastic vulcanizate (TPV) includes a blend of curable rubber and a polyolefin (i.e., PP or PE, homopolymers and copolymers). Curable rubbers include EPDM, EP rubber, santoprene, etc. A polyolefin elastomer includes an olefin block copolymer (OBC), such as Infuse made by Dow, where a crystalline phase of a olefin block copolymer acted as hard blocks, and the amorphous block copolymer acted as soft blocks within the same polymer matrix. The following is a summary of odor barrier as measured by oxygen transmission rate at 23° C. per ASTM D3985:

TABLE 1

Odor Barrier Comparison of Various Elastomers without Organoclays or zeolites

|  | Silicone | SBC | TPV | OBC | SBC w/ polyisobutene | SBC w/ polyisobutene and Organoclay |
|---|---|---|---|---|---|---|
| OTR, cc/m²/day, 20 mil thick wall, ASTM D3985 | 37,500 | 2,500-4,500 | 2,500 | 2,500 | 1,000 | 250 |
| Onion Barrier, ISO 8670-3 | Very poor, detectable in 10 minutes | Poor, detectable in 60 minutes | Poor, detectable in 60 minutes | Poor, detectable in 60 minutes | Better, detectable in 120 minutes | Good, not detectable for 8 hrs |

When antiblocking agent, at least 0.1% or more preferably more than 0.5%, was added to a high barrier elastomer formulation containing a SBC thermoplastic elastomer and a liquid polyisobutene, an odor barrier in the range of around 1000 cc/m²/day was achieved for making a non-blocking fecal catheter. This level of odor barrier improvement was confirmed by an onion test per ISO 8670-3 such that the onion odor breakthrough was longer than 120 minutes. Additional barrier improvement was seen in fecal catheter made from PTE containing a SBC thermoplastic elastomer, a liquid polyisobutene, an organoclay. In this example, onion odor breakthrough was longer than 8 hours. The results of both oxygen barrier and onion barrier were shown in Table 1.

Another embodiment of the present invention is a fecal catheter based on a multilayer structure, wherein at least one layer is selected from a high barrier elastomer described above without any antiblocking agent, and at least another skin layer is selected from the group consisting of (1) same high barrier elastomer described above with at least 0.1% of antiblocking agent, or an elastomer alloy with or without the use of antiblocking agent. An elastomer alloy is defined as a blend of two polymer matrixes which are incompatible in a molecular level. The advantage of antiblocking agent is to impart a rough surface so that the catheter is not blocking. The advantage of an elastomer alloy is that the incompatibility in a molecular level creates a roughness on the catheter surface, giving rise to a non-blocking catheter. In addition, common materials to add for an elastomer alloy include, but not limited to, thermoplastic polyurethane (TPU). Due to a more polar structure in TPU, the subsequent converting of an elastomer alloy is easier. Since the majority of the catheter structure is provided by a high barrier elastomer, the odor barrier and the softness is maintained based on the disclosure above. Because both the center layer and the skin layer are elastomers based, the adhesion between the layers of a fecal catheter is sufficiently good.

Besides the addition of anti-blocking agent, cold processing conditions can be utilized to enhance a rough surface of the catheter wall so that the catheter is not blocking. The effect of anti-blocking agent and/or cold processing conditions is a rough surface that could be characterized by surface roughness using a non-contact surface structure analyzer, such as Scanning White Light interferomtry (SWLI), Atomic Force Microscopy (AFM), etc. A non-contact imaging surface structure analyzer based on SWLI is made by Zygo NewView 7300. A non-contact atomic force microscopy can be made by FEI. A typical parameter that has been used to quantify the quality of a surface topography is the surface roughness, which is represented by the arithmetic mean value, Ra. In this invention disclosure, a rough surface with Ra not less than 0.1 µm or preferably not less than 1 µm when antiblocking agent is used with or without a cold processing temperature, resulted in a non-blocking fecal catheter.

An important characteristic about the formulation described in this invention is its ability to be post-extrusion converted, both by welding and adhesive bonding. Greater than 5 N/in adhesive strength and heat weld strength was achieved.

Another embodiment of the present invention is related to the use of organoclays and/or zeolites to improve the odor barrier of the elastomer catheter.

For example, a single layer of catheter can be made from an organoclay-containing elastomer selected from the group consisting of silicone, polyurethane, styrenic block copolymer, thermoplastic vulcanizate, or polyolefin elastomer with a Shore A hardness not more than 60, or more preferably not more than 50. The use of nanocomposite (nanoclays) fillers to improve the odor barrier is not new. The addition of nanocomposite fillers creates the tortuous path for the odor causing compounds; thus improving the odor barrier for the substrate. There are various nanocomposite containing coating, additives, or polymers marketed by various companies, such as Nanocor, Nanoresin, Southern Clays, Nano-X, Inmat, etc. Since nanocomposites are mostly clay based, it is relatively rigid. Therefore, the challenges of using nanocomposite fillers in FMS application are two fold, (1) the difficulty in the wetting and adhesion of the nanocomposite fillers or coating onto the silicone tubing, and (2) the odor barrier property upon flexing. Therefore, the uniqueness of this invention is the formulation of a soft tube with a completely covered, and/or relatively uniformly dispersed nanocomposite containing catheter which would not crack upon flexing. Such a soft nanoclay-containing catheter is characterized with a Shore A hardness not more than 60, or more preferably not more than 50.

Another embodiment of the present invention is related to single layer of catheter made from a zeolite-containing elastomer selected from the group consisting of silicone, polyurethane, styrenic block copolymer, thermoplastic vulcanizate, or polyolefin elastomer with a Shore A hardness not more than 60, or more preferably not more than 50.

The addition of zeolite creates the tortuous paths and sites to adsorb the odor causing compounds; thus improving the odor barrier for the substrate. There are various zeolites marketed by various companies, such as UOP. Since zeolites are hard fillers, they produce rigidity when used. Therefore, the challenges of using zeolites in FMS application are two fold, (1) the difficulty in the wetting and adhesion of the zeolite coating onto the silicone tubing, and (2) the odor barrier property upon flexing. Therefore, the uniqueness of this invention is the formulation of a soft tube with relatively uniform zeolite-containing elastomeric catheter which would not crack upon flexing. Such a soft zeolite-containing catheter is characterized with a Shore A hardness not more than 60, or more preferably not more than 50.

Another embodiment of the present invention is related to an organoclay-containing coating onto an elastomer substrate selected from the group consisting of silicone, polyurethane, styrenic block copolymer, thermoplastic vulcanizate, or polyolefin elastomer with a Shore A hardness not more than 60, or more preferably not more than 50.

Another embodiment of the present invention is related to a zeolite-containing coating onto an elastomer substrate selected from the group consisting of silicone, polyurethane, styrenic block copolymer, thermoplastic vulcanizate, or polyolefin elastomer with a Shore A hardness not more than 60, or more preferably not more than 50.

A series of experiments were conducted as described below. A total of four different nanocomposites were evaluated, two from Southern Clay and two from Nanocor. Two types of coating matrix were used, silicone and polyurethane. The following is a summary of these findings:

Exp. #1: Silicone Coating Consisting of Nanocomposites:

2.5% of the following nanocomposites were added into a two-part silicone made by Nusil 6350, including (1) Southern Clay Cloisite Na+, Hydrated Aluminum Silicate, (2) Southern Clay Cloisite 15 A, Ammonium salts with Bentonite, (3) Nanocor 1.30 E (Octadecyl ammonium surface compatabilized montmorillonite), and (4) Nanocor 1.34 TCN (methyl, bis hydroxyethyl octadecyl ammonium surface compatabilized montmorillonite).

The two-part silicone was applied onto the silicone catheter as a coating, and was then heat cured at 130 deg C for 30 minutes. The coated catheter was then tested for onion odor barrier per ISO 8670-3:2000. About 5 grams of onion was chopped and filled inside a 12 cm long coated silicone tubing (i.e., catheter).

| Nano-composite | None | Cloisite NA+ | Cloisite 15A | Nanocor 1.30E | Nanocor 1.34TCN |
|---|---|---|---|---|---|
| Coating Matrix, Nusil 6350 | Silicone | Silicone | Silicone | Silicone | Silicone |
| Substrate, Dow Corning C6-135 | Silicone | Silicone | Silicone | Silicone | Silicone |
| Onset of Onion Smell | 5 minutes | 45 minutes | 45 minutes | 90 minutes | 60 minutes |

As can be seen, the addition of 2.5% nanocomposites in a silicone coating improves the onion odor barrier in the silicone tubing. The control with a silicone coating had an onset of onion odor outside of the closed silicone tubing at around 5 minutes. This is about the same as the silicone tube without any coating. After a silicone coating consisting of 2.5% nanocomposites was applied onto a silicone tube, the onset of the onion odor was extended to 45-90 minutes.

Exp. #2: Polyurethane Coating Consisting of Nanocomposites, Without Primer:

2.5% of the following nanocomposites were added into a two-part polyurethane made by Smooth-On, Vytaflex 30, including (1) Southern Clay Cloisite Na+, Hydrated Aluminum Silicate, (2) Southern Clay Cloisite 15 A, Ammonium salts with Bentonite, (3) Nanocor 1.30 E (Octadecyl ammonium surface compatabilized montmorillonite), and (4) Nanocor 1.34 TCN (Methyl, Bis Hydroxyethyl Octadecyl Ammonium Surface Compatabilized Montmorillonite).

The two-part polyurethane was applied onto the silicone catheter as a coating, and was then room temperature cured for 6 hours. The coated catheter was then tested for onion odor barrier per ISO 8670-3:2000. About 5 grams of onion was chopped and filled inside a 12 cm long coated silicone tubing (i.e., catheter).

| Nano-composite | None | Cloisite NA+ | Cloisite 15A | Nanocor 1.30E | Nanocor 1.34TCN |
|---|---|---|---|---|---|
| Coating Matrix, Vytaflex 30 | Polyurethane | Polyurethane | Polyurethane | Polyurethane | Polyurethane |
| Primer, Dow Corning 1200 | No | No | No | No | No |
| Substrate, Dow Corning C6-135 | Silicone | Silicone | Silicone | Silicone | Silicone |
| Onset of Onion Smell | 30 minutes | 6 hours | 6 hours | >12 hours | >12 hours |

As can be seen, the addition of 2.5% nanocomposites significantly improves the onion odor barrier. The control with a polyurethane coating, but without any nanocomposites, was able to extend the onset of onion odor outside of the closed silicone tubing from 5 minutes to 30 minutes. After a polyurethane coating consisting of 2.5% nanocomposites was applied onto a silicone tube, the onset of the onion odor was extended to 6-12 hours. Despite of the odor barrier improvement, the coating adhesion was poor.

Exp. #3: Polyurethane Coating Consisting of Nanocomposites, with Primer:

The same set of experiment as Exp. #2 was repeated with the use of a silane primer, Dow Corning 1200. The same level of onion odor improvement was observed. That is, after a polyurethane coating consisting of 2.5% nanocomposites was applied onto a silicone tube primed with a silane, the onset of the onion odor was extended from 30 minutes in the control without any nanocomposites to 6-12 hours. The polyurethane coating stuck well to the silicone tube, and was able to resist the flex.

| Nano-composite | None | Cloisite NA+ | Cloisite 15A | Nanocor 1.30E | Nanocor 1.34TCN |
|---|---|---|---|---|---|
| Coating Matrix, Vytaflex 30 | Poly-urethane | Poly-urethane | Poly-urethane | Poly-urethane | Poly-urethane |
| Primer, Dow Corning 1200 | Yes | Yes | Yes | Yes | Yes |
| Substrate, Dow Corning C6-135 | Silicone | Silicone | Silicone | Silicone | Silicone |
| Onset of Onion Smell | 30 minutes | 6.5 hours | 6 hours | >12 hours | >12 hours |

Exp. #4: Nanocomposites in a Silicone Slab:

2% of Nanocor 1.30 E was added to make into a 1 mm thick (i.e., 40 mil) silicone gel slab, Nusil 6350. Onion barrier was compared on silicone slab with and without the nanocomposite per ISO 8670-3:2000.

|  | 1 mm thick silicone slab without nanocomposites (control) | 1 mm thick silicone slab with 2% Nanocor 1.30E |
|---|---|---|
| Onset of Onion Smell | 5-10 minutes | 60 minutes |

As a result, the addition of 2% of Nanocor 1.30 E improved the onion odor barrier of the silicone slab from 5 minutes to about 60 minutes.

Another embodiment of the present invention is an improved odor barrier fecal catheter, having a Hardness of less than Shore A 60, comprising at least (a) one layer of a silane coupling agent, and (b) at least one layer of nano-composite coating. This formulation, when applied onto a silicone fecal catheter, would result in an oxygen transmission rate no more than 20,000 cc/m2/day, or preferably, no more than 10,000 cc//m2/day, or more preferably no more than 5,000 cc/m2/day. A silicone tube without the use of silane coupling agent and without the nanocomposite coating has an oxygen permeation rate of around 37,500 cc/m2/day. A silicone with the nanocomposite coating, but without the silane coupling agent, has an oxygen permeation rate of close to 30,000-35,000 cc/m2/day due to the lack of bonding. Alternatively, the same formulation can be applied onto a thermoplastic elastomer (TPE) or a polyurethane tubing (PU), having a Hardness of less than Shore A 60, such that the gas barrier is improved to no more than 25,000 cc/m2/day, or preferably, no more than 10,000 cc/m2/day, or more preferably no more than 5,000 cc/m2/day.

The materials described in this invention can be used as a fecal catheter. A fecal pouch is commonly connected to a fecal catheter in use. The same materials described for fecal catheter were used to make a fecal pouch. Similar odor barrier characteristics against oxygen transmission and onion odor shown in Table 1 were obtained in the lab. Thus, besides a fecal catheter, the same material construction could be used for an ostomy pouch.

We claim:

1. A fecal catheter comprising an odor barrier material comprising:
   i) a thermoplastic elastomer selected from the group consisting of a styrenic block copolymer, a thermoplastic vulcanizate, or a polyolefin elastomer;
   ii) an odor barrier modifier selected from polyisobutene, polybutene, or an organoclay; and
   iii) at least 0.1% antiblocking agent selected from the group consisting of essentially inorganic fillers, including silica, talc, clay, and mica; and
   wherein the antiblocking agent imparts an interior rough surface having an arithmetic mean surface roughness (Ra) not less than 0.1 μm, wherein the fecal catheter is non-blocking upon folding and packaging.

2. The fecal catheter of claim 1, wherein the styrenic block copolymer includes styrene-isoprene-styrene (SIS), styrene-butadiene-styrene (SBS), styrene-ethylene/butylene-styrene (SEBS), styrene-ethylene/propylene-styrene (SEPS), or a blend of above.

3. The fecal catheter of claim 1, wherein the thermoplastic vulcanizate includes a blend of curable rubber and a polyolefin.

4. The fecal catheter of claim 3, wherein said polyolefin is polyethylene and polypropylene, including homopolymers and copolymers thereof.

5. The fecal catheter of claim 3, wherein the curable rubber is selected from the group consisting of ethylene propylene diene monomer (EPDM), ethylene propylene rubber, santoprene, and blends thereof.

6. The fecal catheter of claim 1, wherein the polyolefin elastomer includes an olefin block copolymer wherein a crystalline phase of olefin block copolymer acts as hard blocks and an amorphous block copolymer acts as soft blocks.

7. The fecal catheter of claim 1, wherein the organoclay includes montmorillonite clay, smectite clay, intercalated clay, nanoclay, or a mixture of above.

8. The fecal catheter of claim 1, wherein the oxygen barrier transmission rate per ASTM D3985 is 1000 cc/m$^2$/day or less at 23° C.

9. The fecal catheter of claim 1 having a Shore A hardness of 60 or less.

10. The fecal catheter of claim 1, wherein the surface of the fecal catheter can be bonded with an adhesive having an adhesive strength greater than 5 N/in.

11. The fecal catheter of claim 1, wherein the surface of the fecal catheter can be heat welded having a weld strength greater than 5 N/in.

12. A fecal catheter comprising an odor barrier material comprising:
   an elastomer selected from the group consisting of silicone, polyurethane, styrenic block copolymer, thermoplastic vulcanizate or polyolefin elastomer;
   a nanocomposite filler material coated on or present within said elastomer so as to provide an odor barrier;
   said elastomer and nanocomposite forming a soft catheter tube having a Shore A hardness of not more than 60; and
   wherein the fecal catheter comprises an interior rough surface having an arithmetic mean surface roughness (Ra) not less than 0.1 μm, wherein the fecal catheter is non-blocking upon folding and packaging.

13. The fecal catheter of claim 12, wherein said catheter tube does not crack upon flexing.

14. The fecal catheter of claim 12, wherein said tube is extruded and may be converted both by welding and adhesive bonding.

15. A fecal catheter comprising an odor barrier material, comprising an elastomer substrate and zeolite, said elastomer and zeolite forming a soft catheter tube having a Shore A hardness of not more than 60; and wherein the fecal catheter comprises an interior rough surface having an arithmetic mean surface roughness (Ra) not less than 0.1 μm, such that the fecal catheter is non-blocking upon folding and packaging.

16. The fecal catheter of claim 15, wherein the elastomer substrate is selected from the group consisting of silicone, polyurethane, styrenic block copolymer, thermoplastic vulcanizate and polyolefin elastomer.

17. The fecal catheter of claim 15, wherein the zeolite is incorporated into the elastomer substrate.

18. The fecal catheter of claim 15, wherein the fecal catheter resists cracking upon flexing.

19. The fecal catheter of claim 15, wherein the zeolite is incorporated in a coating on the elastomer substrate.

20. A fecal catheter comprising at least 0.1% antiblocking agent such that the antiblocking agent imparts a rough interior surface to prevent catheter blocking upon folding and packaging, and an interior surface with an arithmetic mean surface roughness (Ra) of not less than 0.1 μm, wherein the fecal catheter is non-blocking.

21. The fecal catheter of claim 20, wherein the interior surface roughness is not less than 0.1 μm and does not trap fecal material.

22. The fecal catheter of claim 20, wherein the antiblocking agent is selected from the group consisting of essentially inorganic fillers, including silica, talc, clay, and mica, and any combination thereof.

23. The fecal catheter of any one of claims 1, 12, 15, and 20, wherein the fecal catheter is at least 10 times better in odor barrier than a silicone catheter as measured by oxygen transmission rate per ASTM D3985.

24. The fecal catheter of claim 1, wherein the odor barrier material further comprises tortuous paths and sites to adsorb the odor-causing compounds.

* * * * *